Figure 1:
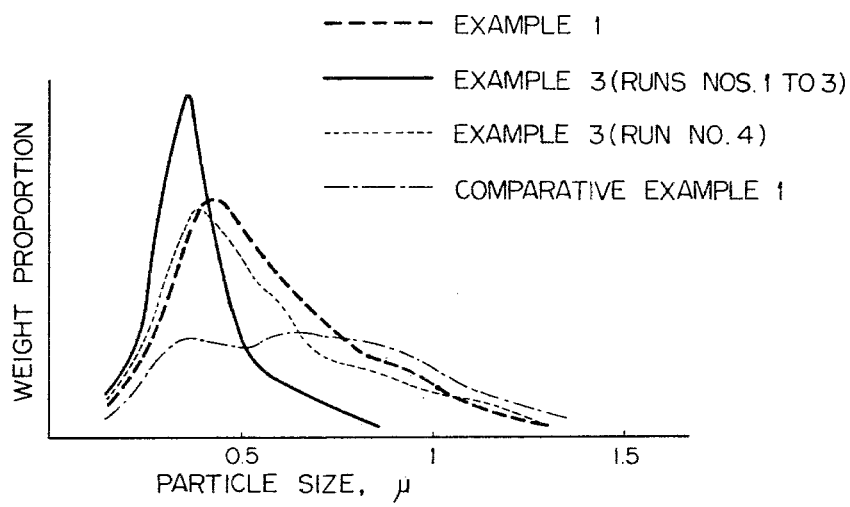

United States Patent [19]

Hayashi et al.

[11] 4,273,723
[45] Jun. 16, 1981

[54] PROCESS FOR PREPARING SILVER SALT OF ORGANIC CARBOXYLIC ACID

[75] Inventors: Yoshio Hayashi; Takeki Matsui; Tetsuo Shiga; Kageyasu Akashi; Minoru Akiyama; Takeo Kimura, all of Fuji, Japan

[73] Assignee: Asahi Kasei Kogyo Kabushiki Kaisha, Osaka, Japan

[21] Appl. No.: 72,852

[22] Filed: Sep. 5, 1979

[30] Foreign Application Priority Data

Sep. 14, 1978 [JP] Japan ................. 53-112363

[51] Int. Cl.$^3$ .............................................. C11C 1/00
[52] U.S. Cl. .................................... 260/414; 430/619; 430/620
[58] Field of Search ................... 260/414, 413 S, 430; 430/619, 620

[56] References Cited

U.S. PATENT DOCUMENTS

| 3,458,544 | 7/1969 | Bryan | 260/430 X |
| 3,839,049 | 10/1974 | Simons | 260/413 S |
| 3,960,908 | 6/1976 | Ikenoue | 260/414 |

Primary Examiner—John F. Niebling
Attorney, Agent, or Firm—Sprung, Felfe, Horn, Lynch & Kramer

[57] ABSTRACT

A process for preparing a silver salt of an organic carboxylic acid comprising reacting an alkali metal salt of the organic carboxylic acid with a water-soluble silver salt, and wherein there is used as the reaction solvent a mixture consisting of at least one water-soluble or partially water-soluble $C_3$–$C_8$ alcohol and water and having a mixing volume ratio of 1/5 to 5/1. The silver salt of the organic carboxylic acid prepared in high yield according to the process of the present invention is in uniformly finely divided form of high purity and suitable for use in photographic materials.

10 Claims, 2 Drawing Figures

PROCESS FOR PREPARING SILVER SALT OF ORGANIC CARBOXYLIC ACID

This invention relates to the preparation of silver salts of organic carboxylic acids. More particularly, this invention relates to a process for preparing a silver salt of an organic carboxylic acid in uniformly finely divided form of high purity.

A silver salt of an organic carboxylic acid is used in essential combination with a reducing agent for silver ion and a photosensitive silver compound or a photosensitive silver compound-forming component capable of forming a photosensitive silver compound by the reaction thereof with part of the silver salt of the organic carboxylic acid to provide a variety of heat-developable photographic materials, examples of which are proposed in U.S. Pat. No. 3,152,904, U.S. Pat. No. 3,457,075 and so on.

The properties of a silver salt of an organic carboxylic acid have significant influences on the essential properties of a photographic material, such as photographic characteristics, e.g., sensitivity, $\gamma$-value, resolution and fogging density, and characteristics of the raw photographic material, e.g., heat stability, moisture resistance and transparency.

Accordingly, various processes for preparing a silver salt of an organic carboxylic acid in finely divided form of high purity have heretofore been proposed, for example, in U.S. Pat. No. 3,458,544, U.S. Pat. No. 3,839,049 and Japanese patent application Laid-Open Specification No. 94619/1974. In U.S. Pat. No. 3,458,544 and Japanese patent application Laid-Open Specification No. 94619/1974, there are proposed processes in which an organic carboxylic acid or a salt of an organic carboxylic acid is emulsified in an aqueous phase in the presence of a water-insoluble or sparingly water-soluble solvent in the preparation of the silver salt of the organic carboxylic acid in finely divided form. In U.S. Pat. No. 3,839,049, there is proposed a process in which a substantially 1:1 by mole mixture of behenic acid and sodium behenate is emulsified in an aqueous phase in the preparation of silver behenate in finely divided form.

However, the above-mentioned processes in which an organic carboxylic acid and/or a salt of the organic carboxylic acid is dispersed in finely divided form in the preparation of the silver salt of the organic carboxylic acid are still unsatisfactory for the preparation of a silver salt of an organic carboxylic acid in uniformly finely divided form of high purity. Especially, in order to obtain a transparent film of a photographic material, a silver salt of an organic carboxylic acid is required to have an average particle size as small as possible, preferably of the order of $0.5\mu$ or less, and also to have a particle size distribution as sharp as possible, preferably such as almost not to contain particles exceeding $1\mu$ in size. The silver salts of the organic carboxylic acids prepared according to the conventional processes do not satisfy such two requirements in respect of average particle size and particle size distribution. Further, when the silver salts of the organic carboxylic acids prepared according to the conventional processes are used as a raw material for the production of photographic materials, the resulting photographic materials are insufficient in resolution and suppression of fogging when they are used for image formation. It is to be noted that even a 1% increase in purity of a silver salt of an organic carboxylic acid contributes to considerable suppression of fogging of photographic materials.

It is therefore an object of the present invention to provide a process for preparing a silver salt of an organic carboxylic acid in uniformly finely divided form of high purity in high yield.

Figure 2:
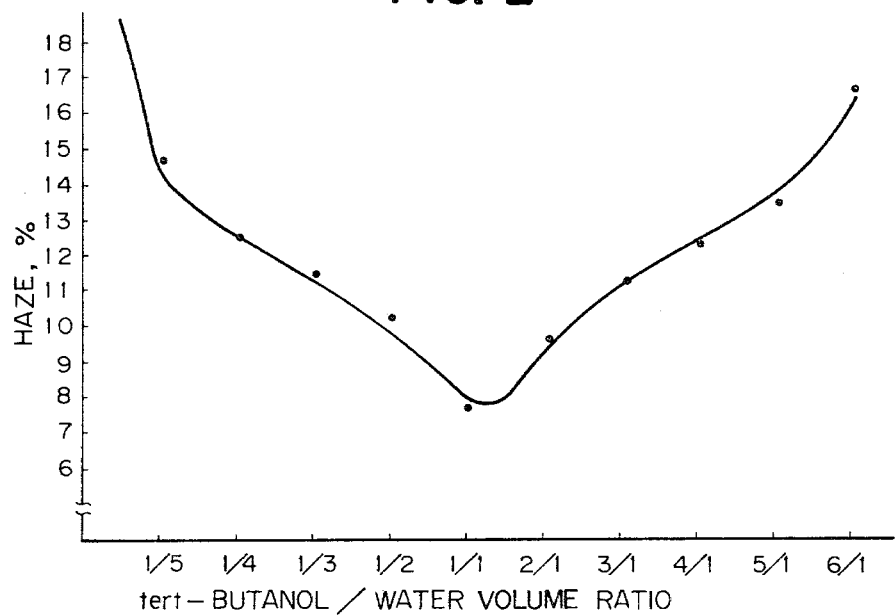

The foregoing and other objects, features and advantages of the present invention will be apparent to those skilled in the art from the following detailed description and appended claims taken in connection with the accompanying drawing in which:

FIG. 1 is a graph showing particle size distributions of silver behenate products, which will be explained later with respect to Example 4 and Comparative Example 2; and FIG. 2 is a graph showing the relationship between the hazes of coated polyester films each comprising a coating layer containing a silver behenate product and the tert-butanol/water volume ratios in the reaction system employed for the production of the silver behenate product, which will be explained later with respect to Example 5 and Comparative Example 3.

We have made intensive investigations for the purpose of solving the problems accompanying the conventional processes, and, as a result, have found that a silver salt of an organic carboxylic acid in uniformly finely divided form of high purity can be prepared in high yield by using as the reaction medium or solvent a mixed solvent consisting of an alcohol and water and having a specific mixing ratio in the reaction of an alkali salt of the organic carboxylic acid with a water-soluble silver salt and that the silver salt of the organic carboxylic acid prepared in the manner described above serves to provide excellent photographic characteristics for photographic materials comprising the same. We have completed the present invention based on such novel findings.

More specifically, in accordance with the present invention, there is provided a process for preparing a silver salt of an organic carboxylic acid comprising reacting an alkali metal salt of the organic carboxylic acid with a water-soluble silver salt, and wherein the reaction is effected in a reaction system comprising (I) the alkali metal salt of the organic carboxylic acid, (II) the water-soluble silver salt, (III) at least one water-soluble or partially water-soluble $C_3$–$C_8$ alcohol and (IV) water, the volume ratio of the component (III) to the component (IV) being 1/5 to 5/1.

The characteristic and essential feature of the present invention resides in the use of a reaction solvent consisting of a mixture of water and a water-soluble or partially water-soluble alcohol solvent. Where such a reaction solvent is used in accordance with the present invention, a precipitate of the silver salt of the organic carboxylic acid separates out from a homogeneous reaction system which is provided by the much increased solubility of the alkali metal salt of the organic carboxylic acid in the reaction solvent with the aid of the water-soluble or partially water-soluble alcohol solvent, whereby the silver salt of the organic carboxylic acid can be prepared in uniformly finely divided form of high purity without being accompanied by impurities. Even if the reaction system is such that it separates into an aqueous phase and an alcoholic phase, the same effect as that achieved in the homogeneous reaction system can be obtained so far as the alcohol is partially soluble in water.

The effect as described above cannot be obtained in a reaction system comprising a water-insoluble or sparingly water-soluble solvent. For example, in the reaction system comprising a sparingly water-soluble solvent as disclosed in Japanese patent application Laid-Open Specification No. 94619/1974, the precipitate of a silver salt of an organic carboxylic acid which separates out from the reaction system is not sufficiently free of impurities and cannot be prepared with good reproducibility of quality.

The specificity of the water-alcohol mixed solvent reaction system can be seen in that the reaction system serves to suitably control the size of the precipitate of a silver salt of an organic carboxylic acid which separates out from the reaction system. In the water-alcohol mixed solvent reaction system, an alkali metal salt of the organic carboxylic acid having strong affinity for the water-alcohol mixed solvent is reacted with a water-soluble silver salt to produce the silver salt of the organic carboxylic acid having substantially no affinity for the water-alcohol mixed solvent, the precipitate of which silver salt is repelled out of the reaction system. Accordingly, the reaction of the alkali metal salt of the organic carboxylic acid dissolved in the mixed solvent with the water-soluble silver salt always proceeds in the mixed solvent reaction system without undergoing an unfavorable influence of the presence of the silver salt product, perhaps contributing to the suitable control of the size of the precipitate of the silver salt product of the organic carboxylic acid.

Water-soluble or partially water-soluble alcohols having 3 to 8 carbon atoms are used as the alcohol component of the mixed solvent to be used in the process of the present invention. The term "partially water-soluble" as used herein is intended to indicate such a solubility that at least 0.1 g of an alcohol is dissolved in 100 g of water under the reaction conditions for practicing the process of the present invention though the alcohol is not completely dissolved in water in any proportions of the alcohol and water. It is preferred in the process of the present invention to use an alcohol capable of dissolving in water in an amount of at least 5 g per 100 g of water. It is most preferred to use an alcohol capable of dissolving in water in any proportions of the alcohol and water.

The alcohol component of the mixed solvent to be used in the process of the present invention is at least one of those alcohols having 3 to 8 carbon atoms. Alcohols having less than 3 carbon atoms cannot serve to provide the aforementioned specificity of the water-alcohol mixed solvent reaction system. On the other hand, alcohols having more than 8 carbon atoms cannot be used in the process of the present invention because of poor solubility in water and/or high viscosity. As representative examples of alcohols to be used in the process of the present invention, there can be mentioned n-butanol, tert-butanol, isobutanol, isopropanol, n-propanol, 1,2-propanediol, 1,3-propanediol, 1,2-butanediol, 1,3-butanediol, 1,4-butanediol, 2,3-butanediol, glycerin, diethylene glycol, dipropylene glycol, triethylene glycol, 2,5-hexanediol, 2-hexanol, 2-pentanol, 3-pentanol, 1,5-pentanediol, pentaglycerol, 3-ethylpentanol, n-octanol and 2-octanol. Of these alcohols, n-butanol, tert-butanol, isobutanol, isopropanol and diethylene glycol are more preferred.

The reaction solvent to be used in the process of the present invention is a mixture of water and an alcohol, which mixture has a mixing volume ratio of 1/5 to 5/1, preferably ½ to 2/1, at which a silver salt of an organic carboxylic acid in uniformly finely divided form of high purity is obtained. The mixing volume ratio of the mixed reaction solvent as specified above is intended to represent a ratio of the component (III) to the component (IV) in the reaction system comprising all of the essential components, i.e. (I) the alkali metal salt of the organic carboxylic acid, (II) the water-soluble silver salt, (III) at least one water-soluble or partially water-soluble $C_3$–$C_8$ alcohol and (IV) water.

An alkali metal salt of an organic carboxylic acid is substantially dissolved in a mixture of at least one water-soluble or partially water soluble $C_3$–$C_8$ alcohol and water to prepare a solution or dispersion containing said alkali metal salt of the organic carboxylic acid whose amount is, for example, 0.01 to 0.5 mole per 1 liter of the abovementioned mixture. In the case of use of a partially water-soluble alcohol as the alcohol component of the reaction solvent, a dispersion may be prepared. The preparation of the above-mentioned solution or dispersion may be made according to any mode or manner. Water, the alcohol and the alkali metal salt of the organic carboxylic acid may be charged in any charging order. Also, the organic carboxylic acid may be mixed with such a mixture as mentioned above and reacted with an alkali metal hydroxide or the like to be converted into the alkali metal salt of the organic carboxylic acid, whereby a solution or dispersion containing said alkali metal salt of the organic carboxylic acid is prepared.

Preferred alkali metal salts of an organic carboxylic acid that are used in the process of the present invention include the potassium salt and the sodium salt. Suitable organic carboxylic acids from which the alkali metal salts of the organic carboxylic acids that are used in the process of the present invention are prepared include long chain fatty acids preferably having 12 to 24 carbon atoms, such as behenic acid, stearic acid, palmitic acid, myristic acid, lauric acid, oleic acid and arachidic acid.

Water-soluble metal salts to be reacted with the alkali metal salt of the organic carboxylic acid include inorganic silver salts such as silver nitrate, silver perchlorate and silver sulfate. Silver nitrate is most preferred.

An alkali metal salt of an organic carboxylic acid to be used in the process of the present invention is substantially dissolved in a mixture of at least one water-soluble or partially water soluble $C_3$–$C_8$ alcohol and water to prepare a solution or dispersion into which a water-soluble silver salt is then added thereby to obtain the desired silver salt of the organic carboxylic acid. In reacting the alkali metal salt of the organic carboxylic acid with the water-soluble silver salt, the reaction conditions are not particularly restricted. The water-soluble silver salt is usually dissolved in water or a mixture of water and at least one water-soluble or partially water-soluble $C_3$–$C_8$ alcohol to prepare a solution of said water-soluble silver salt whose amount is, for example, 0.01 to 10 mole per 1 liter of water or the above-mentioned mixture. The solution of the water-soluble silver salt is then added to the solution or dispersion containing the alkali metal salt of the organic carboxylic acid. The manner and rate of addition of the solution of the water-soluble silver salt and the rate of stirring are not critical and need not to be taken special care of. Alternatively, the solution or dispersion containing the alkali metal salt of the organic carboxylic acid may be added to the solution of the water-soluble silver salt. The reaction temperature is not particularly critical, but may be preferably in the range of from 0° C. to 70° C., more preferably in the range of from 20° C. to 60° C. The reaction period of time is also not critical and may be varied depending upon the scale of the reaction, the manner and rate of addition of the solution of the water-soluble silver salt and the rate of stirring and the like, but may usually be in the range of from 1 second to 1 hour. The amount of the alkali metal salt of the organic carboxylic acid in the reaction system may be 0.005 to 0.5 mole per 1 liter of the total reaction medium or solvent. A simple reaction vessel equipped with an agitating blade may be employed in practicing the process of the present invention.

When the problem of removal of impurities is taken into consideration, it is preferred that the amount of the water-soluble silver salt be substantially equimolar with the amount of the alkali metal salt of the organic carboxylic acid. However, it is possible to use the alkali metal salt of the organic carboxylic acid in a molar amount of up to 5 mole %, preferably up to 0.5 mole %, based on the water-soluble silver salt, in excess of the molar amount of the water-soluble silver salt and to use the water-soluble silver salt in a molar amount of up to 20 mole %, preferably up to 5 mole %, based on the alkali metal salt of the organic carboxylic acid, in excess of the molar amount of the alkali metal salt of the organic carboxylic acid.

A silver salt of an organic carboxylic acid which can provide more excellent photographic characteristics for photographic materials comprising the same can be prepared according to the following preferred mode of the process of the present invention. An alkali metal hydroxide is added in molar excess of the molar amount of an organic carboxylic acid to a mixture of the organic carboxylic acid, at least one water-soluble or partially water-soluble alcohol and water to prepare a solution or dispersion containing the alkali metal salt of the organic carboxylic acid and a surplus of the alkali metal ion. A water-soluble silver salt is added to such a solution or dispersion to effect the reaction between the alkali metal salt of the organic carboxylic acid and the water-soluble silver salt. In this case, the reactivity of the alkali metal salt of the organic carboxylic acid with the water-soluble silver salt is so high that the reaction can proceed sufficiently. In order to sufficiently enhance the reactivity of the alkali metal salt of the organic carboxylic acid with the water-soluble silver salt thereby to effect the reaction sufficiently, the solution or dispersion containing the alkali metal salt of the organic carboxylic acid is desired to be so prepared that the amount, in terms of gram ion, of the alkali metal ion is 0.05 to 2%, preferably 0.1 to 1%, based on the organic carboxylic acid group, in excess of the amount of the organic carboxylic acid group. This preferred mode of the process of the present invention is significant not only in that the yield of the silver salt of the organic carboxylic acid can be increased but also in that there can be obtained a precipitate of the silver salt of the organic carboxylic acid which is substantially free of the organic carboxylic acid and has a sharper particle size distribution.

According to another preferred mode of the process of the present invention, there is prepared a silver salt of an organic carboxylic acid which can provide very excellent storage stability for photographic materials containing the same. A water-soluble silver salt is dissolved in water or a mixture of water and at least one water soluble or partially water-soluble $C_3$–$C_8$ alcohol to prepare a solution of the water-soluble silver salt into which an inorganic acid is added in such an amount that the pH value of the reaction mixture obtained after the reaction between an alkali metal salt of an organic carboxylic acid and the water-soluble silver salt is in the range of from 2 to 6, preferably in the range of from 4 to 5. Inorganic acids that may be added to the solution of the water-soluble silver salt include nitric acid, sulfuric acid, phosphoric acid, perchloric acid and the like. Nitric acid is preferred.

A combination of the above-mentioned two preferred modes of the process of the present invention is more preferred.

The wet cake of a silver salt of an organic carboxylic acid prepared according to the process of the present invention and filtered off from the reaction mixture may be used as a raw material for the production of photographic materials. If desired, the silver salt of the organic carboxylic acid may be washed with water and sufficiently rid of the solvent by centrifugal filtration, drying or the like, and then used as a raw material for the production of photographic materials.

In practicing the process of the present invention, an anti-foggant, a sensitizer, a stabilizer, a sensitizing dye and/or other additives known in the art may be added to the reaction system to prepare a silver salt of an organic carboxylic acid containing the same which can provide desired photographic characteristics for photographic materials comprising the same.

The following Examples illustrate the present invention in more detail but should not be construed as limiting the scope of the invention.

EXAMPLE 1

90.4 g of behenic acid and 2,000 ml of tert-butanol were charged into a 10 liter separable flask and heated to about 60° C. to prepare a solution of behenic acid dissolved in tert-butanol. 265 ml of a 1 N aqueous solution of sodium hydroxide (the amount of sodium hydroxide is equimolar with the amount of behenic acid) were added little by little to the solution of behenic acid to obtain a mixture containing a precipitate of sodium behenate. About 3,000 ml of warm water were added at a stroke to the above-mentioned mixture and the resulting mixture was stirred until the sodium behenate was completely dissolved in the tert-butanol-water system. Thereafter, the mixture was cooled to about 30° C. and 2,660 ml of a 0.1 N aqueous solution of silver nitrate was added at a stroke to the mixture while stirring. The stirring was continued for about 15 minutes. The silver behenate was filtered off, sufficiently washed with water and dried in vacuo. The yield of silver behenate was 97.3% which indicated that the reaction proceeded substantially quantitatively. The purity of the silver behenate product obtained was as extremely high as 98.1%, which is a value obtained by calculation from the silver content of the silver behenate (hereinafter also, the purities of the products are values obtained by the same calculation).

EXAMPLE 2

Substantially the same procedures as described in Example 1 were repeated except that 75.2 of stearic acid were used instead of 90.4 g of behenic acid and 1,800 ml of diethylene glycol were used instead of 2,000 ml of tert-butanol, to obtain silver stearate. The yield of silver stearate was 96.3%. The purity of the silver stearate product obtained was as extremely high as 99.93%.

COMPARATIVE EXAMPLE 1

About 30.7 g of sodium behenate was added to about 500 ml of pure water and the resulting mixture was heated to about 80° C. to prepare a solution of sodium behenate dissolved in water. The solution was gradually cooled to about 75° C. (just before the precipitation of sodium behenate started), and 90 ml of a 1 N aqueous solution (about 55° C.) of silver nitrate was dropwise added, with stirring, to the solution of sodium behenate over a period of about 15 minutes to obtain a precipitate of silver behenate. The yield of silver behenate was as low as 87%. The purity of the silver behenate product obtained was as considerably low as 95.3%.

APPLICATION EXAMPLE 1

With respect to each of the silver behenate product obtained in Example 1, the silver stearate product obtained in Example 2 and the silver behenate product obtained in Comparative Example 1, 2 g of the product were added to 15 g of a 15% by weight solution of polyvinyl butyral in methyl ethyl ketone, and the resulting mixture was stirred by means of a stirrer for about 30 minutes and allowed to stand overnight. There were obtained three kinds of silver salt dispersions to be used for the preparation of photographic emulsions, without using a special dispersing apparatus such as a ball mill.

To each of the silver salt dispersions were added 0.02 g of a solution of mercuric acetate in methanol (a solution obtained by dissolving 20 mg of mercuric acetate into 1 ml of methanol), 0.2 g of calcium bromide, 0.7 g of phthalazinone and 1.5 g of 2,2'-methylenebis(6-tert-butyl-4-ethylphenol) to prepare a homogeneous photographic emulsion.

Each photographic emulsion was coated on a 100 μ-thick polyester film to obtain a photosensitive material having a 18 μ-thick dry coating layer.

Each of the photosensitive material prepared using the silver behenate product obtained in Example 1 and the photosensitive material prepared using the silver stearate product obtained in Example 2 had a smooth surface, and, when it was imagewise exposed for about ⅛ second to light from a 150 watt tungsten lamp and heated at 120° C. for 5 seconds, there was formed thereon an uniformly black image having an optical density of more than 1 and a resolution of more than 250 lines/mm. With respect to the photosensitive material prepared using the silver behenate product obtained in Example 1, the minimum optical density (fogging density) was 0.08. With respect to the photosensitive material prepared using the silver stearate product obtained in Example 2, the minimum optical density was 0.10.

On the other hand, the photosensitive material prepared using the silver behenate product obtained in Comparative Example 1 had a coarse surface because of the poor dispersion of the silver behenate product in the coating layer, and, when it was imagewise exposed for about 1 second to light from a 150 watt tungsten lamp and heated at 120° C. for 5 seconds, there was formed thereon a nonuniform dotted black image having a resolution of less than 60 lines/mm, the unexposed portion of which image had a slightly blackish color and an optical density of 0.31 because of occurrence of fogging, thus indicating that the particles of the silver behenate product have unfavorable properties for use in photographic materials.

EXAMPLE 3

Substantially the same procedures as described in Example 1 were repeated except that a 1 N aqueous solution of sodium hydroxide was used in an excessive amount as indicated in Table 1 with the exception of Run No. 4 and nitric acid was added in an amount as indicated in Table 1 to a 0.1 N aqueous solution of silver nitrate, to obtain silver behenate.

TABLE 1

| Run No. | Surplus NaOH * (mole %) | Amount of HNO₃ ** (mole %) | pH of reaction mixture | Yield (%) | Purity (%) |
|---|---|---|---|---|---|
| 1 | 0.5 | 1 | 3.7 | 99.3 | 99.9 |
| 2 | 0.5 | 0.6 | 4.8 | 99.5 | 99.8 |
| 3 | 0.1 | 1 | 3.4 | 99.2 | 99.8 |
| 4 | 0 | 1 | 2.9 | 93.1 | 98.1 |

Note
* : based on the behenic acid used
** : based on the behenic acid used

As is apparent from Table 1, the yield and purity of behenic acid were notably high in Runs Nos. 1,2 and 3.

EXAMPLE 4 AND COMPARATIVE EXAMPLE 2

The particle size distribution of each of the silver behenate products obtained in Examples 1 and 3 and Comparative Example 1 was determined using an automatic particle analyzer PA-101 (trade name of an automatic particle analyzer manufactured by Union K.K., Japan). In calculation, the specific gravity of silver behenate was assumed to be 1.4. The results were as shown in FIG. 1. The particle size distributions of the silver behenate products prepared in Runs Nos. 1 to 3 of Example 3 were substantially identical to one another and extremely sharp as compared with those of the other products. The particle size distributions of the silver behenate products prepared in Example 1 and Run No. 4 of Example 3 were remarkably sharp as compared with that of the silver behenate product prepared in Comparative Example 1.

EXAMPLE 5 AND COMPARATIVE EXAMPLE 3

Substantially the same procedures as described in Example 1 were repeated except that 4,000 ml of tert-butanol were used instead of 2,000 ml of tert-butanol and the amount of warm water was changed to give, in the reaction system, a tert-butanol/water volume ratio (water: warm water+water in the aqueous solution of sodium hydroxide+water in the aqueous solution of silver nitrate) as is seen in FIG. 2, to obtain silver behenate, the uniformity and fineness of particles of which were then evaluated as follows.

1 g of the silver behenate product obtained was suspended in 9 ml of a 15% by weight solution of polyvinyl butyral in a mixed solvent of toluene and methyl ethyl ketone (mixing volume ratio=1:2) and the resulting suspension was subjected to ultrasonic vibration to prepare a homogeneous dispersion. The dispersion was coated on a 100 μ-thick polyester film at an orifice of 4 mils, followed by drying, and a 10% by weight solution of polymethyl methacrylate in methyl ethyl ketone was coated thereon at an orifice of 2 mils, followed by drying, to prepare a coated polyester film. The haze of the coated polyester film was measured by using an automatic color and color difference meter manufactured by Toyo Rika Kogyo K.K., Japan.

The results were as summarized in FIG. 2, in which the hazes of the coated polyester films are plotted against the tert-butanol/water volume ratios in the reaction systems respectively employed for the production of the corresponding silver behenate products to the respective coated polyester films prepared therefrom.

In general, when a material having a haze of 15% or less is observed with naked eyes, the material gives a feeling of excellent transparency. When a material having a haze of 10% or less is observed with naked eyes, the material gives a feeling of extremely excellent transparency. The haze of a photographic material which haze has close relations with the particle size and dispersibility of a silver behenate product is a significant yardstick in evaluating the influences of the silver behenate product on the appearance of the photographic material, the sharpness of an image formed on the photographic material and ease in practical duplication (which is related to the ultraviolet rays transmittance of the photographic material) when the photographic material is used as a microfilm.

In view of the above, the silver behenate products prepared in the reaction systems having tert-butanol/water volume ratios of 1/5 to 5/1 gave hazes of less than 15% that are excellent in feeling of transparency, and the silver behenate products prepared in the reaction systems having tert-butanol/water volume ratios of ½ to 2/1 gave hazes of about 10% or less that are extremely excellent in feeling of transparency. Thus, it will be easily understood that the silver behenate products prepared according to the process of the present invention will assure the production of excellent photographic materials.

COMPARATIVE EXAMPLE 4

Substantially the same procedures as described in Example 1 were repeated except that 2,000 ml of ethanol were used instead of 2,000 ml of tert-butanol and the addition of a 0.1 N aqueous solution of silver nitrate was carried out at varied temperatures.

The precipitate of sodium behenate in the mixture comprising the ethanol and the water including about 3,000 ml of warm water could not be completely dissolved in the ethanol-water system until the mixture was heated to a temperature as high as 80°–85° C., and the dissolved silver behenate began to precipitate when the mixture was cooled to about 65° C.

When the addition of a 0.1 N aqueous solution of silver nitrate was carried out at 80° C., the yield of silver behanate was as considerably high as 96%. However, the silver behenate product obtained was unsuitable as a raw material for use in photographic materials because a photosensitive material prepared using this silver behenate product in the same manner as in Application Example 1 formed thereon an image having a high fogging density when subjected to imagewise exposure to light and heat development in the same manner as in Application Example 1. This silver behenate product had an appearance of something like welded particles and was poor in dispersibility.

When the addition of a 0.1 N aqueous solution of silver nitrate was carried out at 55° C., the precipitation of silver behenate was accompanied by the entanglement of the sodium behenate and, hence, the purity of the silver behenate product obtained was as low as 94.7%. Further, the silver behenate product did not assume a pure white appearance but a slightly blackish appearance. This silver behenate product was unsuitable as a raw material for use in photographic materials because a photosensitive material prepared using the silver behenate product in the same manner as in Application Example 1 was poor in photographic characteristics and gave an image having an extremely high fogging density when subjected to imagewise exposure to light and heat development in the same manner as in Application Example 1.

EXAMPLE 6

100.2 g of lauric acid and 2,800 ml of isopropanol were charged into a 10 liter separable flask and heated to about 60° C. to prepare a solution of lauric acid dissolved in isopropanol. 505 ml of a 1 N aqueous solution of potassium hydroxide were added little by little to the solution of lauric acid to obtain a mixture containing potassium laurate. About 2,000 ml of warm water (55° C.) were added to the above-mentioned mixture to completely dissolve the potassium laurate in the isopropanol-water system. To the resulting mixture was added at a stroke a mixture of 5,000 ml of a 0.1 N aqueous solution of silver nitrate and 10 ml of a 1 N aqueous solution of nitric acid while stirring. The stirring was continued for about 10 minutes to sufficiently effect the reaction. The silver laurate as the reaction product was filtered off, sufficiently washed with a mixed solvent of water and acetone (mixing volume ratio=1:1) and dried in vacuo. The yield of silver laurate was as high as 99.5% and the purity of the silver laurate obtained was as high as 99.7%.

EXAMPLE 7

111.2 g of sodium laurate, 3,000 ml of n-butanol and 2,000 ml of water were charged into a 10 liter separable flask and heated at 55° C. for about 30 minutes to dissolve the sodium laurate in the n-butanol-water system. To the mixture were added 7 ml of a 1 N aqueous solution of sodium hydroxide. To the resulting mixture was added at a stroke a mixture of 5,000 ml of a 0.1 N aqueous solution of silver nitrate and a 9 ml of a 1 N aqueous solution of nitric acid while stirring. The stirring was continued for about 15 minutes to sufficiently effect the reaction. The silver laurate as the reaction product was filtered off, sufficiently washed with a mixed solvent of water and acetone (mixing volume ratio=1:1) and dried in vacuo. The yield of silver laurate was as high as 99.4% and the purity of the silver laurate obtained was as high as 99.8%.

EXAMPLE 8

Substantially the same procedures as described in Example 6 except that 2,800 ml of n-octanol was used instead of 2,800 ml of isopropanol, to obtain silver laurate. The yield of silver laurate was as high as 99.0% and the purity of the silver laurate obtained was as high as 98.9%.

COMPARATIVE EXAMPLE 5

Silver behenate was prepared in accordance with the process as disclosed in U.S. Pat. No. 3,458,544.

A 0.01 molar solution of behenic acid in benzene was heated to 60° C. This solution was homogenized in an equal volume of water at 60° C. until the emulsion had an average particle size of 1 to 10µ. To the resulting oil-in-water emulsion an equivalent stoichiometric amount of 0.1 N aqueous silver ammonium nitrate solution having a pH of about 9 was added with stirring. The precipitate formed was allowed to settle, filtered using suction, washed with distilled water until the filtrate was free of nitrate ions, and then dried in vacuo. The yield of silver behenate was 97.2% and the purity of the silver behenate obtained was 96.1%.

Using this silver behenate product, a coated polyester film was prepared in substantially the same manner as described in Example 5 and Comparative Example 3. The haze of the coated polyester film was as very high as 19%, thus indicating that the particles of the silver behenate product had unfavorable properties for use in photographic materials.

EXAMPLE 9

Substantially the same procedures as described in Example 1 were repeated except that a mixture of 1,200 ml of isopropanol and 1,000 ml of isobutanol was used instead of 2,000 ml of tert-butanol, to prepare silver behenate. The yield of silver behenate was as high as 98.0% and the purity of the silver behenate obtained was as high as 98.6%.

What is claimed is:

1. A process for preparing a silver salt of a fatty acid with 12 to 24 carbon atoms consisting essentially of reacting an alkali metal salt of the fatty acid with a water-soluble silver salt, and wherein the reaction is effected in a reaction system consisting essentially of (I) the alkali metal salt of the fatty acid, (II) the water-soluble silver salt, (III) at least one water-soluble or partially water-soluble $C_3$–$C_8$ alcohol and (IV) water, the volume ratio of the component (III) to the component (IV) being 1/5 to 5/1.

2. A process according to claim 1, wherein said volume ratio of the component (III) to the component (IV) is ½ to 2/1.

3. A process according to claim 1 or 2, wherein the water-soluble silver salt is silver nitrate.

4. A process according to claim 1, wherein the alkali metal salt of the fatty acid is dissolved in a mixture of at least one water-soluble or partially water-soluble $C_3$–$C_8$ alcohol and water to prepare a solution or dispersion, and the water-soluble silver salt is added to the resulting solution or dispersion to form the reaction system.

5. A process according to claim 1, wherein the reaction system contains the same alkali metal ion as that of the alkali metal salt of the fatty acid in an amount, in terms of gram ion, of 0.05 to 2%, based on the fatty acid group, in excess of the amount of the fatty acid group.

6. A process according to any of claims 1 or 4, wherein the water-soluble silver salt is used in the form of a solution thereof and the solution is so controlled with an inorganic acid that the pH value of the reaction mixture obtained after the reaction between the alkali metal salt of the fatty acid and the water-soluble silver salt is in the range of from 2 to 6.

7. A process according to claim 6, wherein the inorganic acid is nitric acid.

8. A process according to any of claims 1, 2 and 4, wherein said at least one water-soluble or partially water-soluble $C_3$–$C_8$ alcohol is selected from isopropanol, n-butanol, isobutanol, tert-butanol and diethylene glycol.

9. A process according to any of claims 1, 2, 4 and 5, wherein the reaction is carried out at a temperature of 0° to 70° C.

10. A process according to claim 9, wherein the reaction is carried out at a temperature of 20° to 60° C.

* * * * *